United States Patent
Akhlaghi et al.

(10) Patent No.: US 10,307,486 B2
(45) Date of Patent: Jun. 4, 2019

(54) SURFACE MODIFIED NANOCRYSTALLINE CELLULOSE AND USES THEREOF

(71) Applicant: Celluforce Inc., Montreal (CA)

(72) Inventors: Seyedeh Parinaz Akhlaghi, Waterloo (CA); Kam Chiu Tam, Waterloo (CA); Richard M. Berry, Quebec (CA)

(73) Assignee: Celluforce Inc., Montreal, Quebec (CA)

( * ) Notice: Subject to any disclaimer, the term of this patent is extended or adjusted under 35 U.S.C. 154(b) by 0 days.

(21) Appl. No.: 15/245,883

(22) Filed: Aug. 24, 2016

(65) Prior Publication Data

US 2017/0128577 A1 May 11, 2017

Related U.S. Application Data

(63) Continuation of application No. 14/419,147, filed as application No. PCT/CA2013/050555 on Jul. 17, 2013, now abandoned.

(60) Provisional application No. 61/679,297, filed on Aug. 3, 2012.

(51) Int. Cl.
| | |
|---|---|
| *A61K 8/73* | (2006.01) |
| *A61K 9/51* | (2006.01) |
| *A61K 47/38* | (2006.01) |
| *A61Q 11/00* | (2006.01) |
| *A61Q 17/00* | (2006.01) |
| *A61Q 19/00* | (2006.01) |
| *C08B 15/00* | (2006.01) |
| *C08B 15/04* | (2006.01) |
| *C08B 15/06* | (2006.01) |
| *A23L 29/262* | (2016.01) |
| *A23L 29/281* | (2016.01) |
| *A61K 31/245* | (2006.01) |

(52) U.S. Cl.
CPC ............ *A61K 47/38* (2013.01); *A23L 29/262* (2016.08); *A23L 29/281* (2016.08); *A61K 8/731* (2013.01); *A61K 8/736* (2013.01); *A61K 9/5161* (2013.01); *A61K 31/245* (2013.01); *A61Q 11/00* (2013.01); *A61Q 17/005* (2013.01); *A61Q 19/00* (2013.01); *C08B 15/00* (2013.01); *C08B 15/04* (2013.01); *C08B 15/06* (2013.01); *A61K 2800/413* (2013.01); *A61K 2800/57* (2013.01); *A61K 2800/612* (2013.01)

(58) Field of Classification Search
CPC ............ A61K 8/73; A61K 9/51; A61K 47/38
See application file for complete search history.

(56) References Cited

FOREIGN PATENT DOCUMENTS

| WO | 2010105357 A1 | 9/2010 |
|---|---|---|
| WO | 2012068670 A1 | 5/2012 |

OTHER PUBLICATIONS

Peng et al. (The Canadian Journal of Chemical Engineering 9999:1-16 (2011).*
Saito et al. (Biomacromolecules 2007, 8, 2485-2491).*
Thanh et al.( Nano Today (2010) 5, 213-230).*
Johnson (Doctorial Thesis Aug. 18, 2010, Tempo-Oxidized nanocellulose).*
Dhar (Thesis: Novel cellulose nanoparticles for cosmetics and pharmaceutical (2010)).*
Araki, J., et al., Steric Stabilization of a Cellulose Microcrystal Suspension by Poly (ethylene glycol) Grafting, Langmuir, vol. 17(1), 2001, pp. 21-27, American Chemical Society.
Azzam, F. et al., Preparation by Grafting Onto, Characterization, and Properties of Thermally Responsive Polymer-Decorated Cellulose Nanocrystals, Biomacromolecules, vol. 11(12), 2010, pp. 3652-3659, American Chemical Society.
Bulpitt, P., et al., New strategy for chemical modification of hyaluronic acid: preparation of functionalized derivatives and their use in the formation of novel biocompatible hydrogels, Journal of Biomedical Materials Research, vol. 47(2), Nov. 1999, pp. 152-169, John Wiley & Sons, Inc.
Chae, S.Y. et al., Deoxycholic acid-conjugated chitosan oligosaccharide nanoparticles for efficient gene carrier, Journal of Controlled Release, vol. 109(1-3), 2005, pp. 330-344, Elsevier.
Gilles, M.A. et al., Stability of Water-Soluble Carbodiimides in Aqueous Solution, Analytical Biochemistry, vol. 184, 1990, pp. 244-248, Academic Press, Inc.
Isogai, A. et al., TEMPO-oxidized cellulose nanofibers, Nanoscale, vol. 3(1), 2011, pp. 71-85, The Royal Society of Chemistry.
Khutoryanskiy, V.V., Advances in Mucoadhesion and Mucoadhesive Polymers, Macromolecular Bioscience, vol. 11(6), 2011, pp. 748-764, Wiley-VCH GmbH & Co.
Nakajima, N. et al., Mechanism of Amide Formation by Carbodiimide for Bioconjugation in Aqueous Media, Bioconjugate Chemistry, vol. 6, 1995, pp. 123-130, American Chemical Society.
Pieper, J.S. et al., Development of tailor-made collagen-glycosaminoglycan matrices: EDC/NHS crosslinking, and ultrastructural aspects, Biomaterials, vol. 21, 2000, pp. 581-593, Elsevier.
Rånby, B. G., III. Fibrous Macromolecular Systems, Cellulose and Muscle: The Colloidal Properties of Cellulose Micelles, Discussions of the Farday Society, vol. II, 1951, pp. 158-164, The Royal Society of Chemistry.
Rossi, S. et al., Thermally sensitive gels based on chitosan derivatives for the treatment of oral mucositis, European Journal of Pharmaceutics and Biopharmaceutics, vol. 74, 2010, pp. 248-254, Elsevier.

(Continued)

Primary Examiner — Shirley V Gembeh
(74) Attorney, Agent, or Firm — Taft Stettinius & Hollister LLP

(57) ABSTRACT

The present disclosure relates to surface modified nanocrystalline cellulose (NCC) prepared by chemical modification of NCC as well as its use thereof, including as carrier of particular chemical compounds. The surface of nanocrystalline cellulose (NCC) was modified with chitosan oligosaccharide ($CS_{OS}$) by selectively oxidizing the primary alcohol moieties of NCC followed by coupling of the amino groups of $CS_{OS}$ to the oxidized NCC to provide the desired material (NCC-$CS_{OS}$).

11 Claims, 2 Drawing Sheets

(56) References Cited

OTHER PUBLICATIONS

Sam et al., Semiquantitative study of the EDC/NHS activation of acid terminal groups at modified porous silicon surfaces, Langmuir, vol. 26(2), 2010, pp. 809-814, American Chemical Society.

Saito, T., et al., TEMPO-mediated oxidation of native cellulose. The effect of oxidation conditions on chemical and crystal structures of the water-insoluble fractions, Biomacromolecules, vol. 5, 2004, pp. 1983-1989, American Chemical Society.

Sonia, T.A., et al., Chitosan and its Derivatives for Drug Delivery Perspective, Advanced Polymer Sciences, vol. 243, Apr. 2011, pp. 23-54, Springer-Verlag Berlin Heidelberg.

Akhlaghi, S., et al., Comparative release studies of two cationic model drugs from different cellulose nanocrystal derivatives, European Journal of Pharmaceutics and Biopharmaceutics, vol. 88, 2014, pp. 207-215, Elsevier B.V.

Jackson, J., et al. The use of nanocrystalline cellulose for the binding and controlled release of drugs, International Journal of Nanomedicine, vol. 6, 2011, pp. 321-330, Dove Medical Press Ltd.

* cited by examiner

SURFACE MODIFIED NANOCRYSTALLINE CELLULOSE AND USES THEREOF

This application is continuation of U.S. application Ser. No. 14/419,147, which was filed on Feb. 2, 2015 and is a U.S. national stage application under 35 U.S.C. § 371 of International Application No. PCT/CA 2013/050555, which has an international filing date of Jul. 17, 2013, designates the United States of America, and claims the benefit of U.S. Provisional Patent Application No. 61/679,297, which was filed on Aug. 3, 2012. The disclosures of each of these prior applications are hereby expressly incorporated by reference herein in their entirety.

FIELD OF THE DISCLOSURE

The present disclosure relates to surface modified nanocrystalline cellulose (NCC) prepared by chemical modification of NCC as well as its use thereof, including as carrier of particular chemical compounds.

BACKGROUND OF THE DISCLOSURE

The potential of materials derived from natural sources are being extensively investigated, as they find many applications.

Cellulose fiber is the most abundant renewable material. It contains amorphous and crystalline domains. The acid hydrolysis of cellulose fiber disrupts its amorphous domains and releases individual rod-like rigid crystallites called nanocrystalline cellulose (NCC) that possess high mechanical strength. It is known that the treatment of native cellulose with sulphuric acid introduces negative charges to its surface due to the formation of sulphate ester groups. Since the first discovery of NCC in 1949 by Rånby (Rånby G. *Fibrous macromolecular systems cellulose and muscle: the colloidal properties of cellulose micelles*. (1951) Discuss Farday soc, IV(111), pp 158-164), interest in this system has risen particularly over the last decade because of its availability, high surface area and aspect ratio. NCC is also practically non-toxic, biocompatible and biodegradable which makes it a potential candidate for several applications.

Chitosan (CS) is produced from partial deacetylation of chitin, the second most abundant biopolymer in nature. Two marine crustaceans (shrimp and crabs) are the main sources of chitin. CS is an amino polysaccharide that possesses positive charges in acidic media due to the protonation of its amino groups. CS is also practically non-toxic, biocompatible and biodegradable. In pharmaceutics, CS has been widely used as a coating material, disintegrant, tablet binder and a vehicle for peptide and gene delivery. In addition, CS has antimicrobial, haemostatic, wound healing, and mucoadhesive properties (see Sonia, T. A., & Sharma, C. P. *Chitosan and Its Derivatives for Drug Delivery Perspective*. Advanced Polymer Sciences, (2011) 243(April), pp 23-54). Due to its bioadhesive properties, it is known to increase the absorption of drugs from the mucosal membranes by increasing the residence time in the mucous and enhancing the permeability of drugs (see Khutoryanskiy V.V. *Advances in mucoadhesion and mucoadhesive polymers*. Macromolecular bioscience, (2011) 11(6), pp 748-64). Despite the attractive functional properties of CS making it suitable for many uses, there are some problems associated with its in vivo applications, such as high viscosity, high molecular weight, large aggregation formation and low solubility at physiological pHs (7.2-7.4) (see Rossi et al. *Thermally sensitive gels based on chitosan derivatives for the treatment of oral mucositis*. European journal of pharmaceutics and biopharmaceutics: Official Journal of Arbeitsgemeinschaft für Pharmazeutische Verfahrenstechnik e.V, 74(2) (2010), pp 248-54).

SUMMARY OF THE DISCLOSURE

An aspect of the disclosure relates to a surface modified nanocrystalline cellulose (NCC) comprising chitosan oligosaccharides ($CS_{OS}$) covalently bound to the external surface of said NCC (NCC-$CS_{OS}$).

A further aspect of the disclosure relates to a method for preparing a surface modified nanocrystalline cellulose (NCC) comprising oxidizing primary hydroxyl groups of said NCC to provide oxidized functional groups and covalently bounding chitosan oligosaccharides ($CS_{OS}$) to the oxidized functional groups.

Still a further aspect of the disclosure relates to a pharmaceutically, cosmetically or agriculturally active agent comprising the NCC-$CS_{OS}$ as defined herein and a pharmaceutically, cosmetically or agriculturally active chemical compound loaded on said NCC-$CS_{OS}$.

DESCRIPTION OF THE DRAWINGS

The present disclosure is illustrated with reference to the following drawings, in which.

DETAILED DESCRIPTION OF THE DISCLOSURE

Figure 1:
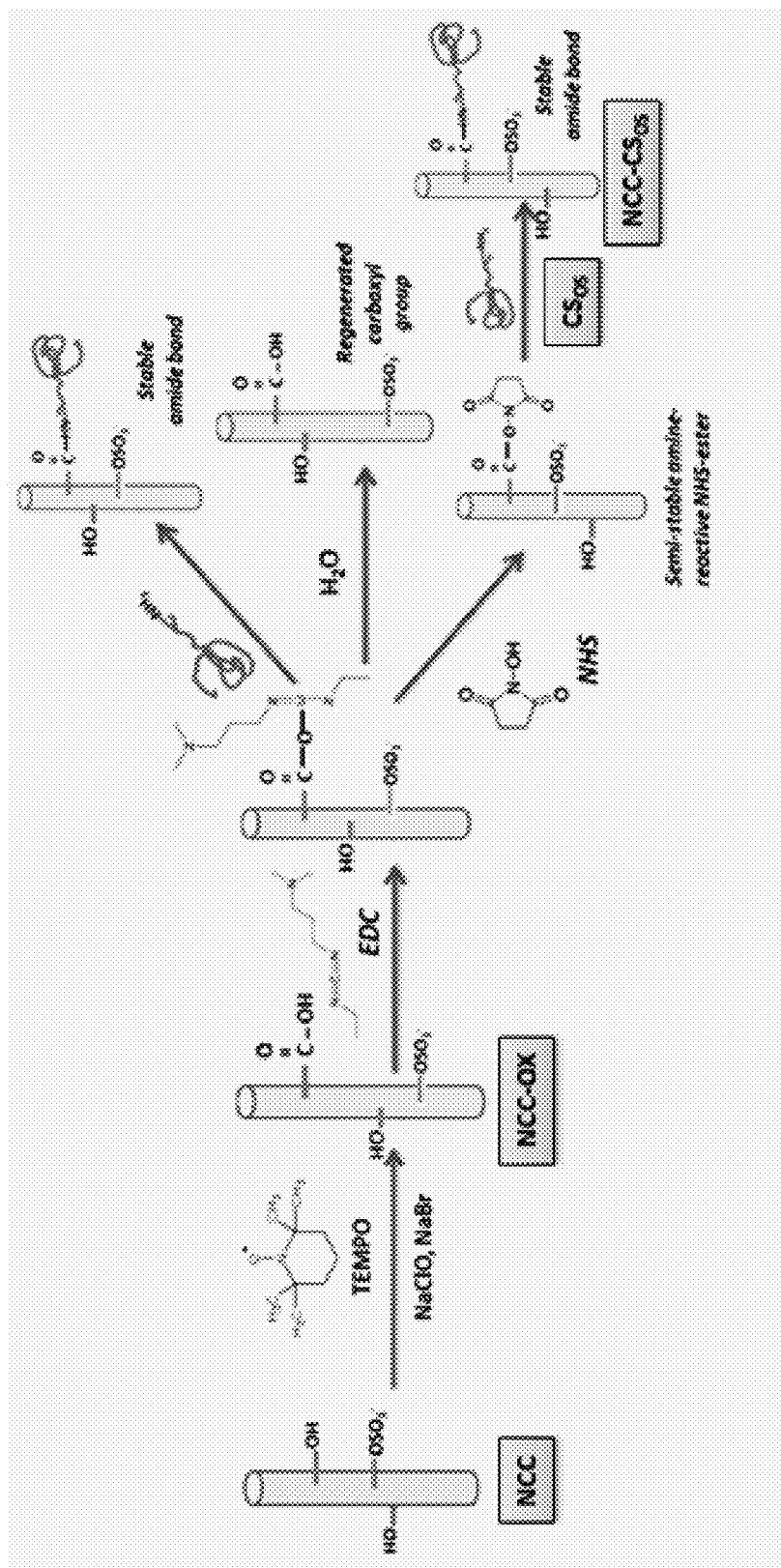
FIG. 1 is a schematic representation of the mechanism synthesis and chemical structures of NCC-$CS_{OS}$.

There is ongoing research in developing novel carriers to deliver active compounds, in a controlled, non-toxic and safe manner.

No attempts appear to have been made in exploiting the combined advantages of modifying the surface of NCC with CS, and in particular $CS_{OS}$ (NCC-$CS_{OS}$), for delivery applications of active compounds. It is believed that NCC-$CS_{OS}$ will not only act as a carrier, but it may also possess the characteristics of CS such as antibacterial, antioxidant, haemostatic and wound healing properties. This system can have potential applications, such as buccal drug delivery and addressing oral cavity problems.

Considering the properties of NCC and CS, a novel surface modified NCC and process for preparing said surface modified NCC have been identified and it has been determined that such agent may be useful for the delivery of active compounds.

In one aspect, there is provided a surface modified nanocrystalline cellulose (NCC) (referred to as NCC-$CS_{OS}$) comprising chitosan oligosaccharides ($CS_{OS}$) covalently bound to the external surface of said NCC (NCC-$CS_{OS}$).

In a further aspect, there is provided a method for preparing a surface modified nanocrystalline cellulose (NCC) by oxidizing primary hydroxyl groups of said NCC to provide carboxyl functional groups that are covalently bonded to chitosan oligosaccharides ($CS_{OS}$).

The NCC-$CS_{OS}$ has the advantage of increased stability due to the chemical linkage over the prior art relating to systems that are composed of NCC and CS.

The NCC-$CS_{OS}$ can be prepared for example by chemically bonding these through an amide (or peptidic) bond. For example, the primary alcohol moieties of NCC can be selectively oxidized to carboxyl groups with a suitable oxidizing agent. The amino groups of $CS_{OS}$ can then be reacted with the carboxylic acid groups using a suitable coupling agent.

Alternatively the hydroxyl groups on the surface of NCC can be oxidized to aldehyde groups and then reacted with primary amino groups on CS to produce imines (C=N).

NCC can practically be extracted from any biomass. In this case we used kraft bleached pulp. In the examples below NCC was obtained from FPInnovations (Pointe-Claire, Quebec Canada)

Suitable oxidizing agents for oxidizing the primary alcohols of NCC have been described previously (see for example Saito, T., & Isogai, A. *TEMPO-mediated oxidation of native cellulose. The effect of oxidation conditions on chemical and crystal structures of the water-insoluble fractions.* Biomacromolecules, (2004) 5(5), Other oxidizing agents can be used for oxidation of alcohols to carboxylic acids such as sodium or potassium dichromate (VI) acidified with dilute sulphuric acid or ammonium persulfate. However, so far the most commonly used reagent for selectively oxidizing the primary hydroxyl groups of NCC into carboxylic acid is TEMPO catalyst.

A suitable reagent/coupling condition between oxidized NCC and $CS_{OS}$ can be found by the skilled person. For example, the carbodiimide coupling reaction can be suitably applied (see Bulpitt, P., & Aeschlimann, D. *New strategy for chemical modification of hyaluronic acid: preparation of functionalized derivatives and their use in the formation of novel biocompatible hydrogels.* Journal of Biomedical Materials Research (1999) 47(2), pp 152-69).

The carbodiimide reaction seems to be the most practical option for coupling $CS_{OS}$ to NCC-OX. "Very few types of chemical groups are known to provide specific and practical conjugation to carboxylic acids (—COOH). Certain diazomethane and diazoacetyl reagents have been used to derivatize small compounds for analysis by HPLC or for fluorescent labeling. Carbonyldiimidazole (CDI) can be used in non-aqueous conditions to activate carboxylic acids for direct conjugation to primary amines (—$NH_2$) via amide bonds. Carbodiimide compounds provide the most popular and versatile method for labeling or crosslinking to carboxylic acids. The most readily available and commonly used carbodiimides are the water-soluble EDC for aqueous crosslinking and the water-insoluble DCC for non-aqueous organic synthesis." (see http://www.piercenet.com/browse.cfm?fldID=F3305493-0FBC-93DA-2720-4412D198A909.)

Low molecular weight CS, known as chitosan oligosaccharides ($CS_{OS}$) can be used in accordance with the present description. This may provide advantageous profiles having regard to CS (e.g. to address the solubility issues of CS) (see Chae et al. *Deoxycholic acid-conjugated chitosan oligosaccharide nano particles for efficient gene carrier.* Journal of Controlled Release, (2005) 109(1-3), pp 330-344).

Different sources of $CS_{OS}$ are known and/or are commercially available. It is believed that depending on the desired application, other $CS_{OS}$ could be used. In the below examples, $CS_{OS}$ lactate (average Mn~5000, DD~75% purchased from Sigma-Aldrich) was used. The degree of deacetylation was calculated using potentiometric titration based on the concentration of amino groups on $CS_{OS}$, which was determined to be 3.62 mmol/g since 100% deacetylated chitin has 5 mmol/g N.

The degree of substitution (DS) was calculated based on the following method:

The reaction between COOH on NCC-OX with $NH_2$ of $CS_{OS}$ was confirmed by comparing the values of DS and degree of oxidation (DO). In the preparation of NCC-$CS_{OS}$ was added 0.2 g (≡0.32 mmol COOH) of NCC-OX and 0.36 g (≡1.29 mmol $NH_2$) of $CS_{OS}$. After the reaction and dialysis, 0.51 g solid was recovered. The calculated the amino groups on NCC-$CS_{OS}$ was 1.60 mmol of $NH_2$/g (≡0.81 mmol $NH_2$). By subtracting the detected $NH_2$ from the primary amine groups added to the reaction medium, it was concluded that 0.48 mmoles of $NH_2$ have either reacted with COOH or been removed during dialysis. Based on the weight loss after dialysis, it was assumed that 0.05 g (≡0.18 mmol $NH_2$) of $CS_{OS}$ was removed. Therefore, 0.30 mmoles of $NH_2$ and COOH had reacted. Thus, 0.02 mmol of COOH was not converted. Thus, the degree of substitution was calculated based on the Equation below:

$$DS\% = \frac{0.30}{0.32} \times 0.28 \times 100 = 26.25$$

Since the DO was determined to be 0.28, we concluded that most of the COOH groups on NCC-OX had been substituted by $CS_{OS}$ via the formation of amide bonds. The DO value 0.28 means that 28% of the hydroxyl methyl groups on NCC have been oxidized to the corresponding carboxylic acid groups and are thus susceptible for subsequent grafting reactions. Therefore, the maximum grafting density corresponds to the situation where approximately every 1 out of every 3.5 anhydroglucose units in NCC contained a grafted $CS_{OS}$ segment. Since the molar ratio of $NH_2$ in $CS_{OS}$ was 4 times greater than COOH on NCC-OX, this result was not unexpected. Also, small hydrophilic amino groups ($CS_{OS}$) are known to be grafted with higher degrees of substitution due to lower steric hindrance. It should be noted that the measurement of the DS by conductimetry which is based on the decrease in the number of amino groups after reaction with carboxyl groups is an indirect proof of grafting. Therefore, in order to check the covalent nature of the grafting FT-IR spectroscopy was also used.

In this invention, it is desirable that a grafting of at least 60% of the carboxyl groups be obtained.

Active compounds that may be used with NCC-$CS_{OS}$ include, without limitation, pharmaceutically, cosmetically or agriculturally useful compounds.

It is believed that NCC-$CS_{OS}$ can be used for the delivery of a wide range of chemical compounds. It would form hydrophobic interactions with compounds due to its carbon backbone. Also, depending on the pH it can be positively or negatively charged which allows the interaction with cationic and anionic compounds. At low pH, where the amino groups on $CS_{OS}$ are protonated, the particles are positively charged and negatively charged chemicals can be loaded via electrostatic interactions. Increasing the pH, will deprotonate the amino groups and particles will be negatively charged due to the $COO^-$ and $OSO_3^-$ groups. Therefore, the release of the anionic compound would be triggered. The same situation would apply for the loading of cationic chemicals at high pH and triggering the release by decreasing the pH. NCC-$CS_{OS}$ can also form hydrogen bonds with many compounds.

Another aspect, refers to a pharmaceutically, cosmetically or agriculturally active agent comprising the NCC-$CS_{OS}$ as defined herein and a pharmaceutically, cosmetically or agriculturally active chemical compound loaded on said NCC-$CS_{OS}$.

Without being bound to theory, it is believed that active compounds could be loaded in the NCC-$CS_{OS}$ as a result of these particles forming small aggregates due to the networking of CS chains and the active compounds being loaded inside these aggregates. Also, the compounds could be adsorbed on the surface of these particles.

As used herein, "adsorption" or "adsorbed" with reference to the interaction between an active compound and NCC-$CS_{OS}$, means the adhesion of molecules to the surface of NCC-$CS_{OS}$. The exact nature of the adsorption will depend on the active chemical compound but can be based on van der Waals forces or ionic interactions as well as coordination or covalent bonding.

In one embodiment, there is provided a pharmaceutical, cosmetical or agricultural composition comprising a pharmaceutically, cosmetically or agriculturally active compound loaded on said NCC-$CS_{OS}$ in association with one or more acceptable carriers, excipients or diluents, for example conventional excipients such as starch, lactose, white sugar and the like and/or fillers.

In one embodiment, the NCC-$CS_{OS}$ loaded active compound or composition comprising same can be further used in combination with at least one additional active agent.

In order to ensure consistency of release of the active compound, in an embodiment of the present disclosure, the NCC-$CS_{OS}$ comprising loaded active compound and compositions described herein may be in the form of a unit dose. The unit dose presentation forms may be tablets, capsules or other suitable forms for pharmaceutical applications, or in the form of granules or other suitable forms for agricultural applications.

The composition may also be in the form of emulsions, suspension or other suitable liquid forms, or may be presented as a dry product for reconstitution with water or other suitable vehicles before use. Such liquid preparations may or may not contain conventional pharmaceutical, agricultural or cosmetic additives.

The NCC-$CS_{OS}$ loaded active compound and compositions described herein may also conveniently be formulated for cosmetical or pharmaceutical topical application alone or in combination with conventional additives.

In a further embodiment, the present disclosure relates to methodologies for preparing the NCC-$CS_{OS}$ active compound loaded on said NCC-$CS_{OS}$ and compositions as defined herein. For example, the surface of nanocrystalline cellulose (NCC) can be modified with chitosan oligosaccharide ($CS_{OS}$) by selectively oxidizing the primary alcohol moieties of NCC followed by coupling of the amino groups of $CS_{OS}$ to the oxidized NCC to provide the desired material (NCC-$CS_{OS}$). Compositions as defined herein can be prepared by admixing together NCC-$CS_{OS}$ having the active compound loaded together with one or more acceptable carriers, excipients or diluents.

It is believed that the (NCC-$CS_{OS}$) particles could have advantages compared to virgin NCC, including:

The $CS_{OS}$ chains grafted on to the surface of NCC add interesting biological properties such as, mucoadhesion, antibacterial, antioxidant, wound healing and etc. Therefore, NCC-$CS_{OS}$ as a drug carrier would have useful biological properties.

It is expected that the $CS_{OS}$ chains grafted on the surface of NCC will delay the release of active compounds resulting in controlled release carriers.

Depending on the pH, NCC-$CS_{OS}$ particles can be positively or negatively charged allowing the loading of various active compounds via electrostatic interactions. Whereas, NCC is negatively charged.

NCC-$CS_{OS}$ can act as pH responsive particles and the release of the loaded active compounds can be triggered by changing the pH.

EXAMPLE 1

TEMPO Mediated Oxidation of NCC (NCC-OX)

In order to modify NCC with $CS_{OS}$, the surface hydroxyl groups of NCC was initially oxidized to carboxyl groups using NaClO assisted by 2,2,6,6,-tetramethyl-1-(pyperidinyloxy) radical (TEMPO). TEMPO is a stable and water-soluble nitroxyl radical and due to its steric hindrance, it can only oxidize the primary hydroxyl groups on NCC to convert them to carboxylic acids (see above Saito & Isogai, 2004).

In order to disrupt the NCC bundles and obtain a homogenous dispersion, NCC (1.3 g, 8.02 mmol glycosyl units) was dispersed in deionized (D.I.) water (100 ml) and sonicated in a Branson 1510 sonicator (Branson Ultrasonic Corporation, USA) for 10 min. Then, TEMPO (20 mg, 0.128 mmol) and NaBr (400 mg, 3.880 mmol) were added to the NCC suspension and stirred for 30 min at room temperature. The pH of the solution was 5.8, and adjusted to 10 by adding 0.5 M NaOH. The oxidation was initiated by slowly adding NaClO 13% (9.8 ml, 17.114 mmol) over 30 min under gentle agitation. The pH was kept constant at 10, by the continuous addition of 0.5 M NaOH. The reaction was known to be complete when no additional reduction in the pH was observed, which was determined to be approximately 4 hours. Once the reaction was complete, excess oxidant was quenched using methanol (10 ml) and the pH was adjusted to 7 using 0.5 M HCl. In order to purify the oxidized nanocrystals, the solution was dialyzed against distilled water for at least 48 h (see Araki, J. et al. *Steric Stabilization of a Cellulose Microcrystal Suspension by Poly (ethylene glycol) Grafting*. Cellulose, (2001) (17), pp 21-27).

After 1 h of performing the TEMPO mediated oxidation of NCC to NCC-OX with the structure of β-1,4-linked polyglucuronic acid sodium salt (cellouronic acid Na salt), the solution became clear. The cellulose molecules are packed in its crystalline unit cell in a manner where only half of the primary hydroxyl groups (hydroxymethyl) are extended out of the crystalline structure, which are then accessible for oxidation. This is because some cellulose nanocrystals form aggregates due to defects such as twists, kinks and chain ends. It is known that the regioselective oxidation of hydroxyl groups on the surface of NCC to carboxylic acid is due to the fact that half of the cellulose chains on the surface are buried inside the crystalline domains of the nanocrystals whereas the other half on the exterior of the aggregates are available for oxidation. The 1-oxopiperidinium ions on the surface of NCC are accessible for oxidation. The introduction of carboxylic acid groups on the surface of NCC without changing its crystalline structure provides a unique platform for further modification of NCC. By further nano-manipulating of these functional groups, one can create various novel compounds. The conversion of primary hydroxyl groups to carboxylic acids is known to be pH dependent. The pH of the reaction medium also affects oxidation time, and a pH of 10 was shown to result in the shortest oxidation time. At acidic pH values, the secondary hydroxyl group might be oxidized whereas, at pH values higher than 10, the cellulose could be degraded by β-elimination that decreases the molecular weight of the resulting cellulose fibers.

EXAMPLE 2

Grafting of Chitosan Oligosaccharide on NCC

Grafting of $CS_{OS}$ onto NCC-OX, prepared in example 1, was performed according to Bulpitt and Aeschlimann (see Bulpitt, P., & Aeschlimann, D. *New strategy for chemical modification of hyaluronic acid: preparation of functionalized derivatives and their use in the formation of novel biocompatible hydrogels*. Journal of Biomedical Materials Research (1999) 47(2), pp 152-69) with some modifications. Briefly, NCC-OX (0.2 g, 0.32 mmol COOH) was dissolved in 50 ml D.I. water. A 50 ml solution containing 1-ethyl-3-(3-dimethylaminopropyl) carbodiimide (EDC) (0.19 g, 1 mmol) and N-hydroxysuccinimide (NHS) (0.11 g, 1 mmol) was added to the NCC-OX suspension and stirred for 15 min. Another solution containing $CS_{OS}$ (0.36 g, 1.3 mmol $NH_2$) was dissolved in 100 ml D.I. water and then added to the first solution resulting in a 200 ml reaction volume. 2-(N-morpholino)ethanesulfonic acid (MES) buffer (1.95 g, 0.05 M) was added to the reaction medium and the pH was adjusted to 5 using 1 M NaOH or HCl. The reaction was stirred for 24 h at room temperature and purified using a dialysis tube (Mw cut off: 12,000 Da) against D.I. water for 4 days until the conductivity of the dialysis medium remained constant (see Azzam, F. et al. *Preparation by grafting onto, characterization, and properties of thermally responsive polymer-decorated cellulose nanocrystals*. Biomacromolecules (2010) 11(12), pp 3652-9). The grafting resulted in a conversion of greater than 90% carboxyl groups on NCC-OX and the degree of substitution (DS) was 0.26.

NCC-$CS_{OS}$ grafted copolymer was synthesized via the carbodiimide coupling reaction also known as the peptidic coupling reaction. This reaction involves the formation of an amide bond between the amino groups of $CS_{OS}$ and carboxyl groups on NCC-OX in the presence of EDC—an effective amidation reagent and NHS (N-hydroxysuccinimide), an esterification reagent in MES buffer. EDC is a water-soluble carbodiimide and forms amide bonds without a spacer molecule, hence it is known as a "zero-length" cross-linker.

The schematic representation for the synthesis of NCC-$CS_{OS}$ is shown in FIG. 1. For simplicity, only one of the functional groups is illustrated on $CS_{OS}$ and NCC-OX. EDC reacts with the carboxyl groups of NCC-OX forming an amine-reactive ester (O-acylisourea) intermediate. This active ester may further form an amide bond by reacting with primary amino groups on $CS_{OS}$. However, this intermediate is susceptible to hydrolysis and thus, has a short life-time in aqueous solutions. The addition of NHS stabilizes the amine-reactive intermediate by converting it into an amine-reactive NHS-ester. This increases the efficiency of the EDC mediated coupling reaction. The purification of the sample was performed by dialysis against water, where unreacted $CS_{OS}$, EDC and by-product (isourea) were removed.

Different parameters such as, reaction medium, reaction time, pH and molar ratios between the reagents and the crosslinker, could be changed resulting in variations of grafting behaviours (Pieper, J. S. et al. *Development of tailor-made collagen-glycosaminoglycan matrices: EDC/NHS crosslinking, and ultrastructural aspects*. Biomaterials (2000) 21, pp 581-93). In order to minimize the hydrolysis of EDC, crosslinking was conducted in 0.05 M MES buffer at pH 5 (Gilles, M. A. et al. *Stability of water-soluble carbodiimides in aqueous solution*. Analytical Biochemistry (1990) 184, pp 244-248). The choice of pH is very important when using EDC as it affects the coupling efficiency of EDC to COOH groups. However, if the objective is to have well-dispersed particles and fully solubilized reagents, the pH should be chosen to address both issues. The commonly reported optimal range for EDC use is 4-6 (Nakajima N. et al. *Mechanism of amide formation by carbodiimide for bioconjugation in aqueous media*. Bioconjugate Chemistry, (1995) 6, pp 123-130). In our approach, we adjusted the pH to 5, where EDC is not only at its optimal range but also $CS_{OS}$ is fully soluble. Different ratios of COOH, $NH_2$, EDC and NHS have been used in the literature. In this study, the ratios used were as follows: (COOH, 1 mmol): ($NH_2$, 4 mmol): (EDC, 3 mmol):(NHS, 3 mmol). The reason for choosing the $NH_2$ on $CS_{OS}$ to be 4 fold of COOH on NCC-OX was to ensure that all the possible carboxyl groups had sufficient amino groups for grafting (see above Azzam et al.), and the unreacted $CS_{OS}$ could be removed by dialysis. The choice of the ratio of EDC and NHS was based on the work of Sam and co-workers who found that the optimum coupling result was obtained with [EDC]=[NHS]=5 mM (Sam et al. *Semiquantitative study of the EDC/NHS activation of acid terminal groups at modified porous silicon surfaces*. Langmuir, (2010) 26, pp 809-814, 2010).

EXAMPLE 3

Loading of an Active Compound—Procaine Hydrochloride

To a 15 ml of 0.1 wt % NCC-$CS_{OS}$ (obtained from Example 2) suspension was added 15 ml of a solution containing 150 mg procaine hydrochloride (PrHy) and 0.017 g NaCl was added drop-wise to yield a concentration of 18.3 mM PrHy and an ionic concentration of 0.01 M NaCl. The pH of the NCC-$CS_{OS}$-PrHy solution was adjusted to 8 and the solution was stirred for 30 min at 37° C. and equilibrated for 1 h at room temperature. The NCC-$CS_{OS}$-PrHy solution was then passed through the stirred ultrafiltration cell (Millipore Corporation, Bedford, USA) with filters having a cut-off pore size of 25 nm (Millipore, VSWP, Ireland). The concentration of free PrHy in the filtrate was measured using a DSE. EMF measurements were recorded by the titration system with a built-in micro-voltometer. The electrode potential was recorded as a function of PrHy concentration (log [PrHy]) and calculated based on the calibration curves of EMF (mV) against concentration of PrHy on a logarithmic scale from $10^{-4}$ to $10^{-1}$ M.

The binding efficiency of NCC-$CS_{OS}$ and drug loading were determined indirectly by measuring the free drug in the filtrate using the following expressions:

$$BindingEfficiency = \frac{[PrHy]_{total} - [PrHy]_{filtrate}}{[PrHy]_{total}} \times 100$$

$$Drugloading = \frac{\text{Weight of } PrHyloaded}{\text{Weight of } NCC - CS_{OS}}$$

For NCC-$CS_{OS}$, the binding efficiency and drug loading were 21.5% and 14% w/w, respectively. In an earlier study (see Jackson, J. K., et al. *The use of nanocrystalline cellulose for the binding and controlled release of drugs*. International Journal of Nanomedicine (2011) 6, pp 321-330) on the use of virgin NCC as a drug carrier for release studies, similar results were obtained. For tetracycline an ionizable hydrophilic drug, the researchers observed a binding efficiency and drug loading of 25% and 20% w/w, respectively (see Jackson, J. K., et al. —as above).

EXAMPLE 4

In-Vitro Drug Release Studies

Drug release studies were performed at room temperature using a double-walled jacket vessel. For the release studies, 2 ml of the PrHy-loaded NCC-CS$_{OS}$ particles were added to 25 ml D.I. water with an ionic strength of 10 mM NaCl at pH 8 at a constant temperature of 37° C. with gentle stirring at 300 rpm. The in-vitro drug release profile of NCC-CS$_{OS}$ particles was measured using the DSE. The EMF of the bulk solution of the experiment was recorded by the Radiometer ABU93 Tri-burette titration system at a regular interval of 20 s and the values were later converted to concentration values.

Figure 2:
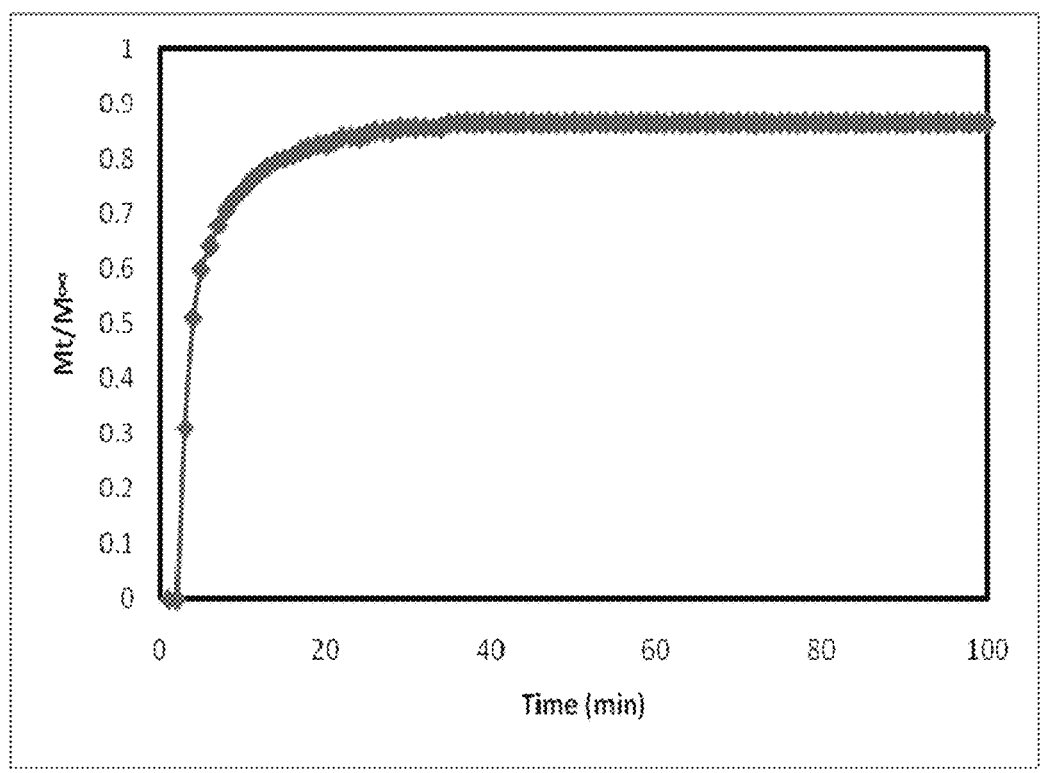
FIG. 2 is a graph demonstrating the in-vitro release profile for procaine hydrochloride from NCC-$CS_{OS}$ particles at pH 8.

FIG. 2 shows the in-vitro release profile of PrHy loaded NCC-CS$_{OS}$ at pH 8. It shows a relatively fast release of PrHy in the first 10 min (burst release) followed by a slower release of the remaining drug in about 1 h. The initial burst release is probably due to the drug on the surface of NCC, while the slower release could be due to the CS$_{OS}$ grafted on the surface of NCC that inhibited the release to some extent due to steric hindrance.

Studies have been conducted on comparing the mixture of NCC-OX and CS$_{OS}$ at the same ratio with covalently bound NCC-CS$_{OS}$ in terms of zeta potential and antioxidant activity. The NCC-CS$_{OS}$ possesses more positive charge and more antioxidant activity. This could be due to the fact that the CS$_{OS}$ polymer chains have been grafted onto NCC they are in a more extended form and hence the amino groups are more accessible. The other possible advantages of the chemical grafting of NCC-CS$_{OS}$ could be the thermal stability and the fact that the particles will have a more coherent structure which will make them favourable for long term in vivo applications.

The ratio of Mt/M∞ is the molar ratio of drugs released at time t and the drugs that partitioned to the NCC-CS$_{OS}$ particles. The drug release profile obtained was comparable to that of the previous study (see Jackson et al., *The use of nanocrystalline cellulose for the binding and controlled release of drugs*. International Journal of Nanomedicine (2011) 6, pp 321-330).

While the disclosure has been described in connection with specific embodiments thereof, it is understood that it is capable of further modifications and that this application is intended to cover any variation, use, or adaptation of the disclosure following, in general, the principles of the disclosure and including such departures from the present disclosure that come within known, or customary practice within the art to which the disclosure pertains and as may be applied to the essential features hereinbefore set forth, and as follows in the scope of the appended claims.

The invention claimed is:

1. A surface modified nanocrystalline cellulose (NCC) comprising chitosan oligosaccharides (CS$_{OS}$) covalently bond to the external surface of said NCC (NCC-CS$_{OS}$).

2. The modified nanocrystalline cellulose (NCC) of claim 1, wherein said covalent bond is a peptide bond.

3. The modified nanocrystalline cellulose (NCC) of claim 1, wherein said covalent bond is an imine (C=N).

4. A pharmaceutically, cosmetically or agriculturally active agent comprising the NCC-CS$_{OS}$ as defined in claim 1 and a pharmaceutically, cosmetically or agriculturally active chemical compound loaded on said NCC-CS$_{OS}$.

5. A pharmaceutical, cosmetical or agricultural composition comprising the pharmaceutically, cosmetically or agriculturally active agent as defined in claim 4 admixed together with one or more acceptable carriers, excipients or diluents.

6. A method for preparing a surface modified nanocrystalline cellulose (NCC) comprising oxidizing primary hydroxyl groups of said NCC to provide oxidized functional groups and covalently bonding chitosan oligosaccharides (CS$_{OS}$) to the oxidized functional groups.

7. The method of claim 6, wherein said primary hydroxyl is oxidized to a carboxyl functional group.

8. The method of claim 7, wherein said primary hydroxyl is oxidized by TEMPO-mediated oxidation sodium or potassium dichromate (VI) acidified with dilute sulphuric acid or ammonium persulfate.

9. The method of claim 7, wherein said covalent bond is obtained by contacting said oxidized primary hydroxyl groups of NCC and said chitosan oligosaccharides (CS$_{OS}$) with a carbodiimide reagent.

10. The method of claim 8, wherein said covalent bond is obtained by contacting said oxidized primary hydroxyl groups of NCC and said chitosan oligosaccharides (CS$_{OS}$) with a carbodiimide reagent.

11. The method of claim 6, wherein said primary hydroxyl is oxidized to an aldehyde functional group.

* * * * *